United States Patent [19]
Jascomb

[11] Patent Number: 6,129,085
[45] Date of Patent: Oct. 10, 2000

[54] CRANIOTOMY DRAPE

[75] Inventor: Jerald T. Jascomb, Alpharetta, Ga.

[73] Assignee: Kimberly-Clark Worldwide, Inc., Neenah, Wis.

[21] Appl. No.: 09/036,362

[22] Filed: Mar. 6, 1998

Related U.S. Application Data

[62] Division of application No. 08/705,698, Aug. 30, 1996, Pat. No. 5,778,889.

[51] Int. Cl.⁷ ..................................................... A61B 19/00
[52] U.S. Cl. ........................... 128/849; 128/852; 128/853
[58] Field of Search .................................... 128/849–856

[56] References Cited

U.S. PATENT DOCUMENTS

| Re. 34,512 | 1/1994 | Dowdy et al. |
| D. 334,457 | 3/1993 | Becker . |
| 3,575,407 | 4/1971 | Carson . |
| 3,650,267 | 3/1972 | Anderson . |
| 3,667,458 | 6/1972 | Krebs . |
| 3,799,161 | 3/1974 | Collins . |
| 3,856,006 | 12/1974 | Krzewinski .......... 128/132 D |
| 3,911,912 | 10/1975 | Krebs et al. . |
| 3,923,052 | 12/1975 | Zoephel . |
| 3,952,738 | 4/1976 | Krzewinski . |
| 3,955,569 | 5/1976 | Krzewinski et al. . |
| 4,007,741 | 2/1977 | Waldrop et al. . |
| 4,036,235 | 7/1977 | Hathaway . |
| 4,041,203 | 8/1977 | Brock et al. . |
| 4,089,331 | 5/1978 | Hartigan et al. . |
| 4,105,019 | 8/1978 | Haswell . |
| 4,201,212 | 5/1980 | Bradley . |
| 4,378,794 | 4/1983 | Collins . |
| 4,384,573 | 5/1983 | Elliott . |
| 4,414,968 | 11/1983 | Amin . |
| 4,457,026 | 7/1984 | Morris . |
| 4,462,396 | 7/1984 | Wichman . |
| 4,465,066 | 8/1984 | Carpel . |
| 4,553,538 | 11/1985 | Rafelson .......... 128/132 D |
| 4,559,937 | 12/1985 | Vinson . |
| 4,569,341 | 2/1986 | Morris . |

(List continued on next page.)

FOREIGN PATENT DOCUMENTS

| 0 166 124A | 1/1986 | European Pat. Off. . |
| 0 268 567A | 5/1988 | European Pat. Off. . |
| 1476674 | 6/1977 | United Kingdom . |
| 2018597 | 10/1979 | United Kingdom . |

OTHER PUBLICATIONS

Groah, Linda K., RN, CNOR, *Operating Room Nursing: The Perioperative Role*, Reston Publishing Co., Inc., Reston, VA, pp. 164–167, 274–280 (1983).

LeMaitre et al., *The Patient in Surgery: A Guide for Nurses*, W.B. Saunders Co., Philadelphia, PA, 3rd ed. pp. 116–117 (1975).

Meeker et al., *Alexander's Care of the Patient in Surgery*, Mosby, St. Louis, MO, 10th ed., pp. 87–92 (1995).

McCredie et al., *Basic Surgery*, Macmillan Publishing Co., New York, NY, 2nd ed., p. 198.

*Primary Examiner*—Michael A. Brown
*Attorney, Agent, or Firm*—Jones & Askew Attys.; Nancy M. Klembus

[57] ABSTRACT

The present invention is a fenestrated craniotomy drape including a main sheet, translucent anesthesia side screens, a gusset forming the corners of the anterior edges of the drape, a run-off collection pouch whose back side is pressed flat and affixed to the drape, with a back side fenestration surrounding the fenestration of the main sheet, and a front side fenestration, and adjustable tube holders. The drape optionally includes a layer of a fenestrated absorbent material between the drape and the pouch, a solids screen and drain port in the pouch, and a ductile material about the edges of the front side fenestration of the pouch that holds the pouch open. The back-side fenestration of the pouch and those of the drape and the absorbent material are covered by an incise sheet, located between the back side of the pouch and the drape. The adhesive side of the incise sheet facing the patient is covered by a releasable backing.

8 Claims, 4 Drawing Sheets

U.S. PATENT DOCUMENTS

| | | |
|---|---|---|
| 4,570,628 | 2/1986 | Neal . |
| 4,586,498 | 5/1986 | Morris . |
| 4,596,245 | 6/1986 | Morris . |
| 4,598,458 | 7/1986 | McAllester . |
| 4,616,642 | 10/1986 | Martin et al. . |
| 4,699,131 | 10/1987 | Crook et al. . |
| 4,730,609 | 3/1988 | McConnell . |
| 4,745,915 | 5/1988 | Enright et al. . |
| 4,869,271 | 9/1989 | Idris . |
| 4,873,997 | 10/1989 | Marshall . |
| 4,889,135 | 12/1989 | Poettgen . |
| 4,890,628 | 1/1990 | Jackson . |
| 4,945,924 | 8/1990 | Poettgen . |
| 4,966,168 | 10/1990 | Glassman . |
| 5,002,069 | 3/1991 | Thompson et al. . |
| 5,038,798 | 8/1991 | Dowdy et al. . |
| 5,042,507 | 8/1991 | Dowdy . |
| 5,107,859 | 4/1992 | Alcorn et al. . |
| 5,127,423 | 7/1992 | Draeger . |
| 5,140,997 | 8/1992 | Glassman . |
| 5,143,091 | 9/1992 | Patnode . |
| 5,161,544 | 11/1992 | Morris . |
| 5,197,493 | 3/1993 | Grier-Idris . |
| 5,209,243 | 5/1993 | Glassman . |
| 5,213,114 | 5/1993 | Bailey, Jr. . |
| 5,222,507 | 6/1993 | Taylor . |
| 5,322,071 | 6/1994 | Ambrose . |
| 5,345,946 | 9/1994 | Butterworth et al. . |
| 5,349,965 | 9/1994 | McCarver . |
| 5,361,780 | 11/1994 | Kellan . |
| 5,361,781 | 11/1994 | Antonini . |
| 5,394,891 | 3/1995 | Mills et al. . |
| 5,398,700 | 3/1995 | Mills et al. . |
| 5,413,118 | 5/1995 | Thompson . |
| 5,419,343 | 5/1995 | Taylor . |
| 5,445,165 | 8/1995 | Fenwick . |
| 5,452,729 | 9/1995 | Bergsbaken et al. . |
| 5,464,024 | 11/1995 | Mills et al. . |
| 5,503,163 | 4/1996 | Boyd . |
| 5,540,979 | 7/1996 | Yahiaoui . |
| 5,709,221 | 1/1998 | Vancaillie et al. ............ 128/894 |

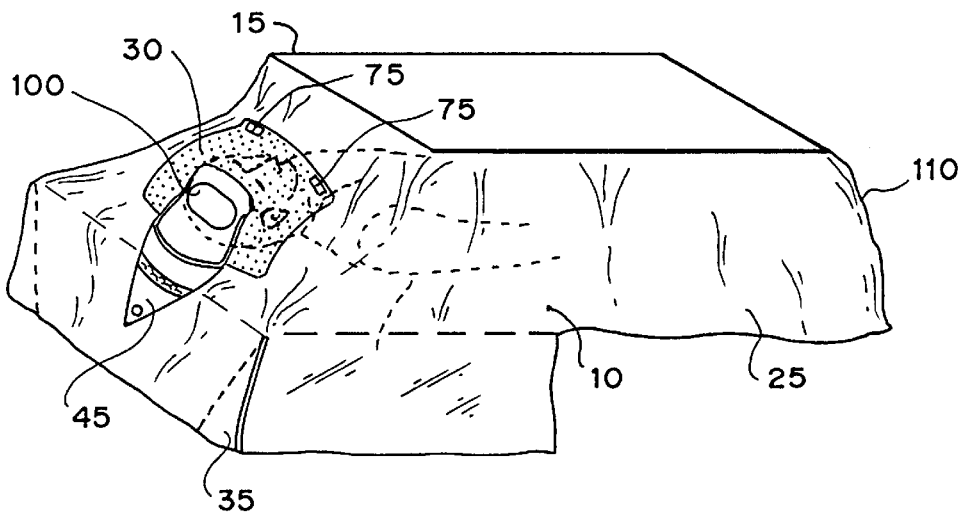
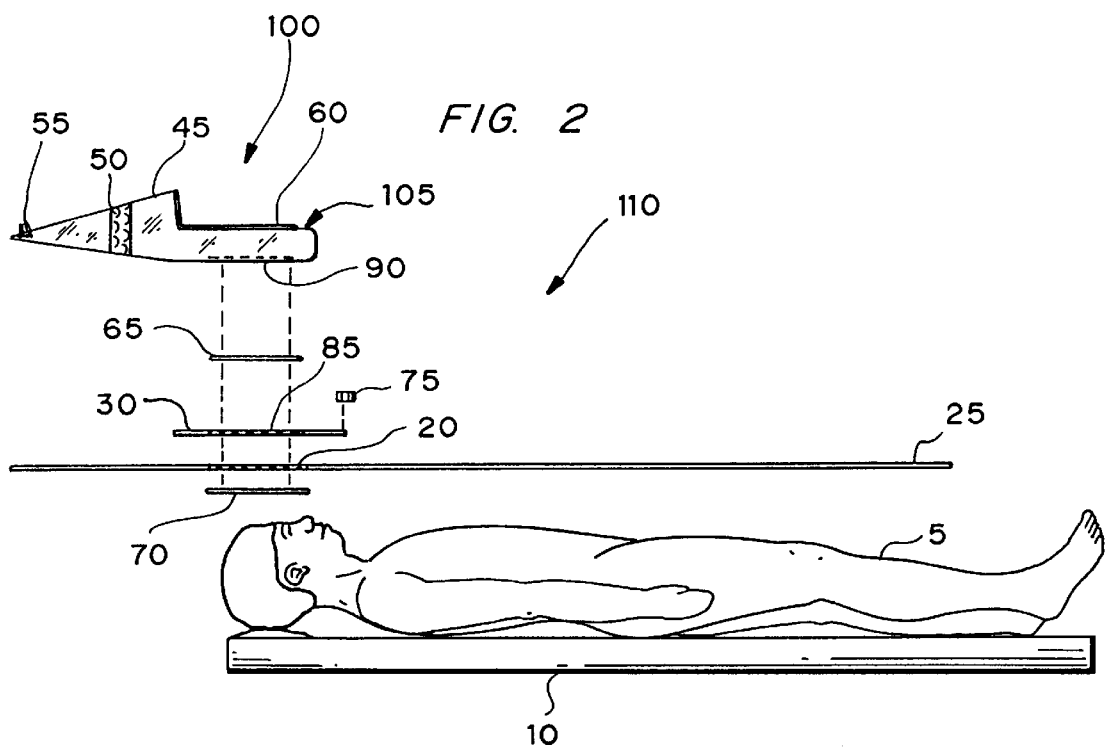

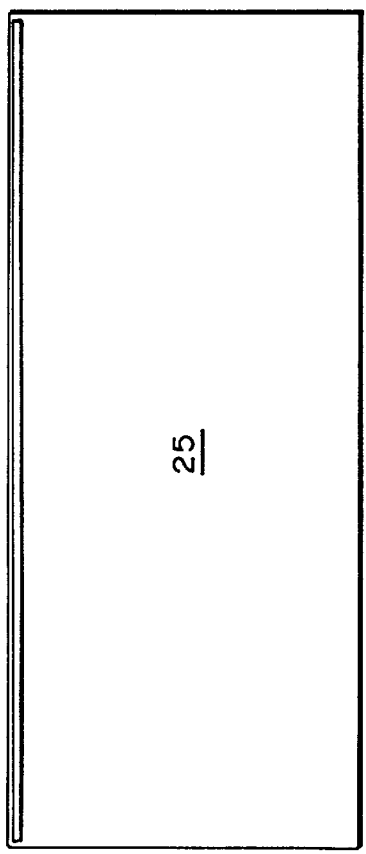
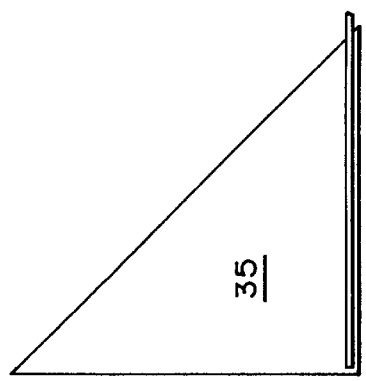
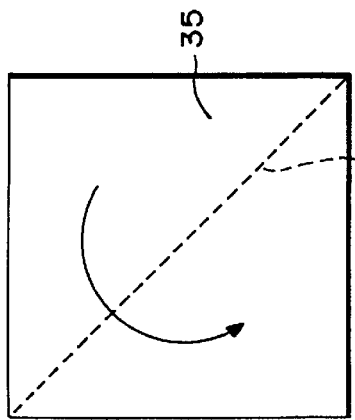
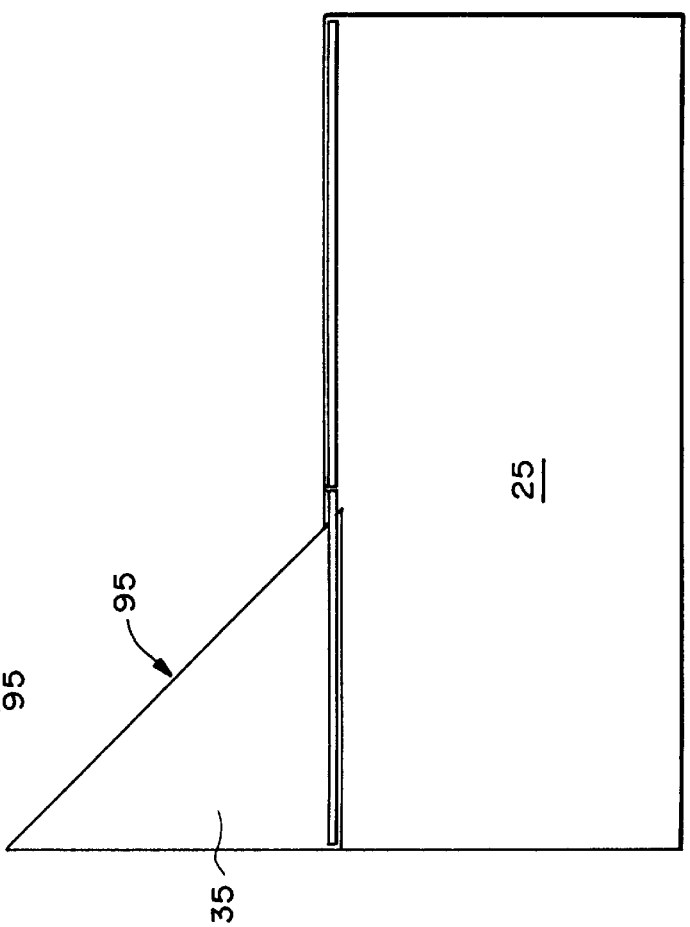
FIG. 4

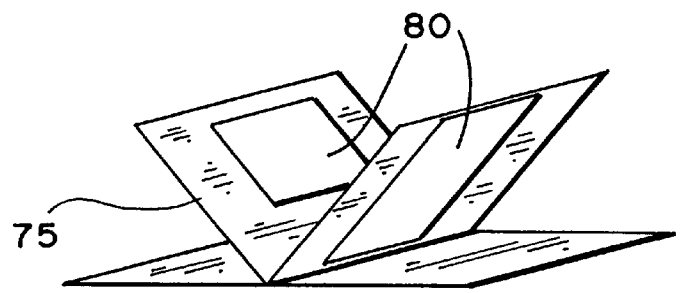
FIG. 5
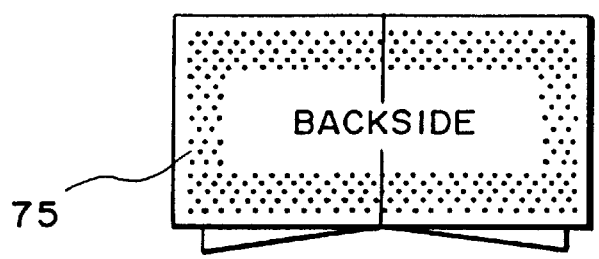
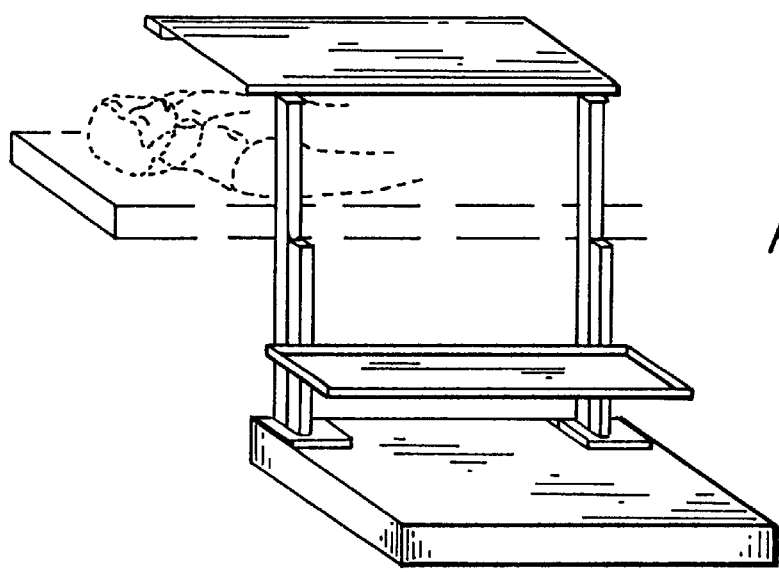
FIG. 6

CRANIOTOMY DRAPE

This application is a divisional of application Ser. No. 08/705,698 entitled CRANIOTOMY DRAPE and filed in the U.S. Patent and Trademark Office on Aug. 30, 1996 now U.S Pat. No. 5,778,889. The entirety of application Ser. No. 08/705,698 is hereby incorporated by reference.

FIELD OF THE INVENTION

The present invention is in the field of surgical drapes, more particularly in the field of craniotomy drapes.

BACKGROUND OF THE INVENTION

Draping procedures create an area of asepsis called a sterile field. All sterile items that come into contact with the prepared area about the wound must be restricted within a defined area of safety to prevent transportation of microorganisms into the open wound. The sterile field is created by placement of sterile sheets and towels, or other draping materials, in a specific position to maintain the sterility of surfaces on which sterile instruments and gloved hands may be placed. The patient and operating room table are covered with sterile drapes in a manner which exposes the prepared site of incision and isolates the area of the surgical wound. Objects draped often include instrument tables, basin and Mayo stands, trays, and some surgical equipment.

Draping materials are selected to create and maintain an effective barrier that minimizes the passage of microorganisms between non-sterile and sterile areas. To be effective, a barrier material should be resistant to blood, drapable. It should maintain an isothermic environment that is appropriate to body temperature. It should meet or exceed the requirements of the current National Fire Protection Standards, so no risk from a static charge exists. *Alexander's Care of the Patient in Surgery*, eds. M. H. Meeker, R. N., et al., 10th edition (Mosby St. Louis, Mo. 1995).

Drapes covering a surface are only considered to be sterile on the side of the drape away from the surface. The portions of the drape hanging down and away from the draped object or person are not considered sterile, since the range of human vision cannot always be counted on to notice breaks in technique and resulting contamination of the drape. p. 117, G. D. LeMaitre, M. D., et al., *The Patient in Surgery: A Guide for Nurses*, 3rd edition (W. B. Saunders Co. Philadelphia 1975).

Neurosurgical tables currently in use are normally located over and slightly above the person on whom the operation is to be performed. The table is usually prepared for the surgical procedure by the placement of one or more drapes, each for a specific purpose, in order to cover the non-sterile table and areas surrounding the head of the patient.

The anesthesiologist in a neurosurgical operation is usually seated to one side or the other of the operating table. It is desirable for the anesthesiologist to observe the face of the patient and the breathing apparatus connected to the patient to properly assess the patient's condition throughout the surgical procedure. Currently, in order to observe the face of the patient, the anesthesiologist either lifts up a corner of the drape, or attaches the drape to an intravenous bottle standpole, so that the face of the patient may be continuously observed. Obviously this presents problems of contamination, as the sterile field is compromised. Furthermore, neurosurgical operations are very long procedures, in which surgeons sit down for portions of time in wheeled chairs, or move about the head area of the patient. Current drapes trail onto the floor, creating accident hazards for operating room personnel as they walk about the table, as well compromising the sterility of the drape.

Electric cords and suction lines running along the patient to the head area are usually clamped or tied to the edges of the outer sheet on the table. These cords or lines can become tangled, and when pulled may cause devices to fall to the floor and become unsterile. This represents a risk to the patient while under a general anesthesia for the period of time required for the preparation of new sterile devices. Furthermore, the clamps and ties are usually not versatile or strong enough to allow easy addition or removal of tubes and electrical lines. This results in delay in surgery while operating room personnel undo and re-affix clamps.

Therefore, it is an object of the present invention to provide a drape where the face of the patient may be observed directly by the anesthesiologist without compromising the sterile field.

It is another object of the invention to provide a drape which does not trail on the floor of the operating room.

It is a further object of the invention to provide clamps on a drape which are strong and easily adjusted.

SUMMARY OF THE INVENTION

The present invention is a fenestrated craniotomy drape including a main sheet, translucent anesthesia side screens, a gusset forming the corners of the anterior edges of the drape, a run-off collection pouch whose back side is pressed flat and affixed to the drape, with a back side fenestration surrounding the fenestration of the main sheet, and a front side fenestration, and adjustable tube holders. The drape optionally includes a layer of a fenestrated absorbent material between the drape and the pouch, a solids screen and drain port in the pouch, and a ductile material about the edges of the front side fenestration of the pouch that holds the pouch open. The back-side fenestration of the pouch and those of the drape and the absorbent material are covered by an incise sheet, located between the back side of the pouch and the drape. The adhesive side of the incise sheet facing the patient is covered by a releasable backing.

BRIEF DESCRIPTION OF THE DRAWINGS

FIG. 1 is a perspective view of the craniotomy drape in use.

FIG. 2 is an exploded cut-away view of the craniotomy drape in use.

FIG. 4 is a top view of the right side of the craniotomy drape showing the gusset before and after folding along the fold line, the anesthesia screen, and the folded gusset attached to the anesthesia screen.

FIG. 5 is a view of the adjustable tube holders.

FIG. 6 is a perspective view of an overhead table and an operating room table with a patient lying on it.

DETAILED DESCRIPTION OF THE INVENTION

Figure 3:
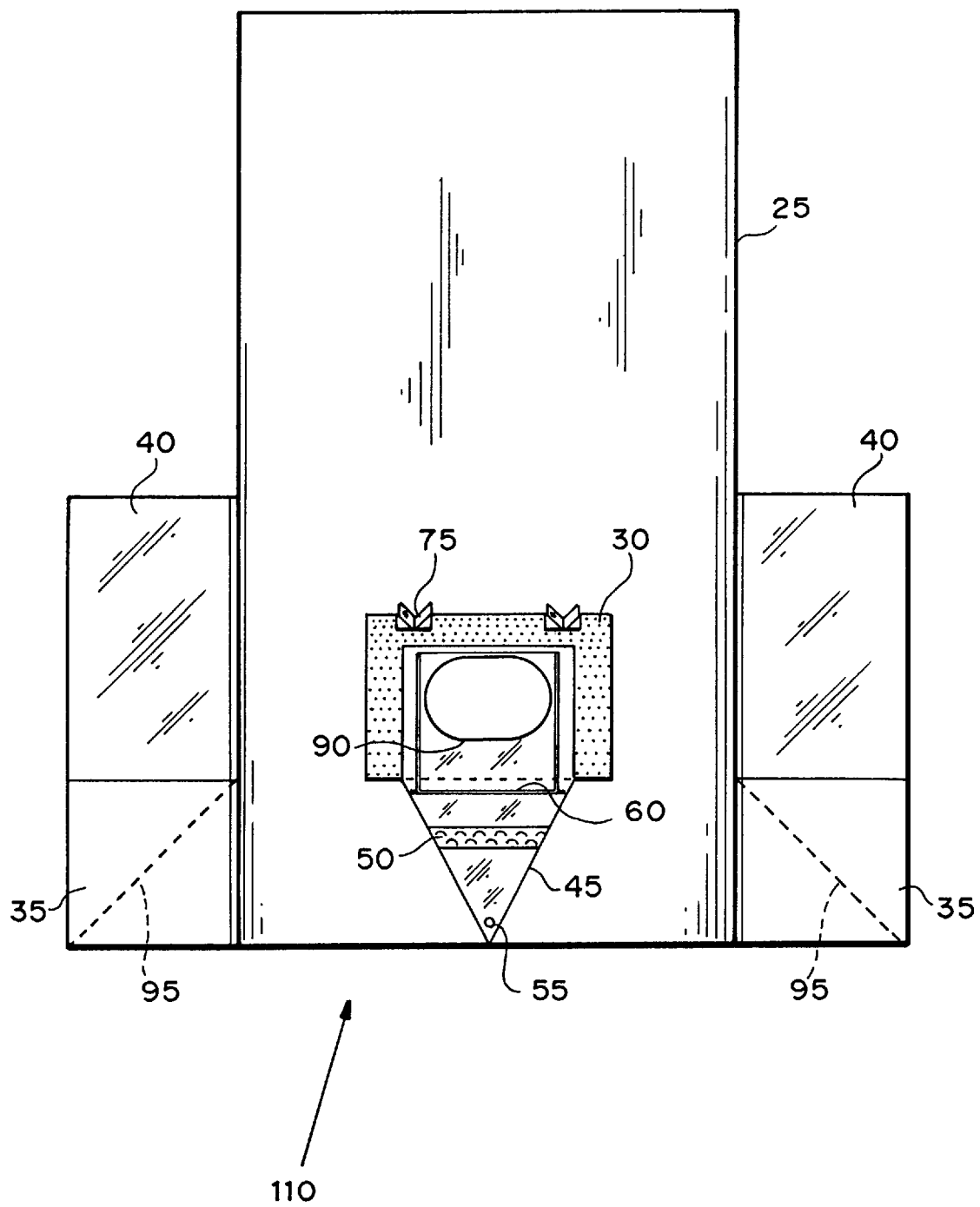
FIG. 3 a top view of the craniotomy drape.

The present invention is a fenestrated craniotomy drape including a main sheet, translucent anesthesia side screens, a gusset forming the corners of the anterior edges of the drape, a run-off collection pouch whose back side is pressed flat and affixed to the drape, with a back side fenestration surrounding the fenestration of the main sheet, and a front side fenestration, and adjustable tube holders. The drape optionally includes a layer of a fenestrated absorbent material between the drape and the pouch, a solids screen and drain port in the pouch, and a ductile material about the edges of the front side fenestration of the pouch that holds the pouch open. The back-side fenestration of the pouch and those of the drape and the absorbent material are covered by an incise sheet, located between the back side of the pouch and the drape. The adhesive side of the incise sheet facing the patient is covered by a releasable backing.

General Description

The craniotomy drape of the current invention, is generally used as illustrated by 110 in FIG. 1. It is draped over a surgical overhead table 15, under which lies a patient 5 undergoing a craniotomy procedure. The drape is designed to collect solids and fluids, such as body fluids and irrigation fluids, that collect during the course of the procedure.

FIG. 2 is an exploded cut-away view of the drape 110. The drape includes a fenestrated main sheet 25, on top of which is an optional fenestrated absorbent sheet 30, and on top of that is secured the flat back side of a fenestrated run-off pouch 45, the fenestration, or hole 90 in the back of which is coincident with the fenestration 85 in the absorbent material and the fenestration 20 in the main sheet 25. An incise sheet 65 is layered between the absorbent sheet 30 and the run-off pouch 45, with a releasable backing 70.

The main sheet 25 may be made from a woven, reusable fabric, but preferably is made from a non-woven, disposable fabric such as EVOLUTION 3® fabric polypropylene SMS. The EVOLUTION fabric is a three-layer laminate of spunbond, meltblown, and spunbond layers (SMS). An example of a suitable fabric is found in U.S. Pat. No. 4,041,203, entitled, "Nonwoven thermoplastic fabric," listing inventors R. J. Brock and G. H. Meitner." This patent is incorporated herein by reference. Referring to FIG. 2, the main sheet 25 should be large enough to cover the patient's body 5. In one embodiment of the invention, the main sheet is approximately 134 inches long by 74 inches wide. The main sheet 25 includes a fenestration 20, positioned toward the anterior portion of the drape. In one embodiment, the fenestration is oval, and placed in the midline about 24 inches from the anterior end of the drape, over the patient's head. The surgical procedure is performed within the fenestration.

On the top side of the main sheet 25 is optionally layered a fenestrated absorbent sheet 30. The fenestration 85 of the absorbent sheet is coincident with or larger than the fenestration 20 of the main sheet 25. In one embodiment, the absorbent sheet is composed of the material claimed in U.S. Pat. No. 5,540,979, to inventors Yahiaoui, A., Potts, D. C., Perkins, C. A., Powers, M. D., and Jascomb, J. T., entitled "Porous non-woven bovine blood-oxalate absorbent structure." This patent is incorporated herein by reference. In one embodiment, the absorbent sheet is approximately 36 inches long by 24 inches wide. In one embodiment, the absorbent sheet 30 is affixed to the main sheet 25 using cold glue.

Tube Holders

One or more adjustable tube holders 75 are secured either to the main sheet 25 or to the absorbent sheet 30 attached to the main sheet. These tube holders, as shown in FIG. 5, are made up of two rectangular pieces of a flexible material joined at a center line like the wings of a bi-plane. In one embodiment of the invention, the material is CONTROL-PLUS™ manufactured by the Kimberly-Clark Corporation, located in Neenah, Wisconsin.

CONTROL-PLUS™ is polypropylene spunbond/ polypropylene meltblown/polyethylene film laminate. The upper piece has a loop and hook fastener arrangement 80 on its outer edges, while the lower piece is secured either to the main sheet 25 of the drape or to the absorbent sheet 30. In one embodiment, the tube holders 75 are affixed using a hot melt. In one embodiment of the invention, the hook and loop fastener is a VELCRO® fastener. In one embodiment of the invention, the upper and lower rectangular pieces are two inches by four inches, the velcro hook piece is one inch by one inch, and the velcro loop is one inch by two inches.

Run-off Pouch

Secured to the absorbent sheet 30, or to the main sheet 25, is a fenestrated run-off pouch 45 to collect fluids and solids generated during surgery (See FIG. 2 and FIG. 3). The run-off pouch 45 is preferably made from a fluid-impervious material, such as translucent polypropylene, and optionally includes a drain port 55, to which a suction apparatus may be attached, and a solids screen 50, so that solids will not block the drain port 55. The back side of the run-off pouch 45 is secured to the optional absorbent sheet or directly to the main sheet 25, and includes a fenestration 90 which is roughly coincident with the fenestrations of the main sheet and the optional absorbent sheet. The back side of the run-off pouch 45 surrounds the fenestration 90 on the back side of the pouch. When in use, the closed end of the pouch hangs down and away from the head of the patient 5.

The fenestration 100 on the front side of the run-off pouch 45 has a ductile material 60 around its borders. The ductile material 60 helps keep the pouch open. In one embodiment of the invention, the ductile material is two parallel metal wires about 0.5 centimeter apart housed in flat plastic, where the plastic is secured to the border of the fenestration 100.

Incise Sheet

Turning now to FIG. 2, layered flat between the back side of the run-off pouch 45 and the main sheet 25, or between the optional absorbent sheet 30 and the main sheet 25, is an incise sheet 65, with the adhesive side facing the patient 5. In one embodiment, the incise sheet 65 is a low-density polyethylene film with adhesive on one side. More preferably, the incise sheet 65 is constructed of polyethylene film made by Bertek Inc., St. Albans, Vt. 05478. The adhesive side is covered with a releasable backing 70. After the releasable backing 70 is removed, the incise sheet 65 is exposed through the main sheet fenestration 20, and will contact the patient 5 when the drape 110 is placed on the patient 5.

Gussets

As shown in FIG. 1, and more particularly in FIG. 3, on each side of the anterior portion of the main sheet 25 are located gussets 35. These may be of the same material as the main sheet 25. The gussets 35 may be made from a woven, reusable fabric, but preferably are made from a non-woven, disposable fabric such as EVOLUTION 3 ® fabric polypropylene SMS. In one embodiment, the gussets are approximately square, and 24 inches by 24 inches. The gussets have a main fold line 95 going diagonally across the gussets 35, which, when the drape is in use, prevent the corners of the drape 110 from trailing on the floor. (See FIG. 4). As shown in FIG. 3 and the lower right quadrant in FIG. 4, the anesthesia screens 40 are translucent, and are connected by their lateral edges to the main sheet 25. The gusset 35 is attached to both the main sheet 25 and the anesthesia screen 40, as illustrated in FIGS. 3 and 4. The lower left quadrant of FIG. 4 shows the anesthesia screen 40 attached to a gusset 35 with the gusset folded along the fold line 95. The upper left quadrant of FIG. 4 shows a gusset laid flat, transversed by a fold line 95 running from one corner of the gusset 35 to the other. The middle right-hand section of FIG. 4 shows the gusset 35 folded along the fold line 95 to form a triangle. In one embodiment, heat-sealable tape 120 may be used to connect the outside edges of the main sheet 25, the gusset 35 and the anesthesia screen 40, as illustrated in the upper right quadrant of FIG. 4. As shown in FIG. 1, the gusset causes the corners of the anterior of the drape 110 to become recessed, which also keeps the corner out of the way of surgical personnel in the operating room. In one embodiment, the fold lines 95 are at approximately a 45 degree angle to the front anterior edge of the drape 110.

Translucent Anesthesia Screens

As shown in FIG. 1, and more particularly in FIG. 3, attached to one or more edges of the anterior portion of the main sheet 25 are one or more translucent anesthesia side screens 40. In one embodiment of the invention, they are approximately rectangular, with dimensions of 30 inches by 56 inches. Preferably, the screens are clear. These side screens may be made of any appropriate translucent plastic, such as clear polyethylene film. These permit the anesthesiologist to view the face of the patient without lifting the drape and compromising the sterile field.

Use of the Drape

The craniotomy drape 110 is taken out of a pack (not shown) and draped over an overhead table 15 (see FIG. 1 and FIG. 6), and over a patient 5 lying on the underlying operating table 10. The releasable backing 70 is peeled away, and the adhesive side of the incise sheet 65 is placed on the area of the patient's head prepared for surgery. The run-off pouch 45 hangs down and away from the head of the patient 5. A suction apparatus (not shown) may be connected to the drain port 55, and various electrical wires and tubes may be secured with the tube holders 75. Surgery is performed directly through the incise sheet 65.

Those skilled in the art will now see that certain modifications can be made to the invention herein disclosed with respect to the illustrated embodiments, without departing from the spirit of the instant invention. While the invention has been described with respect to the illustrated embodiments, it will be understood that the invention is adapted to numerous rearrangements, modifications, and alterations, and all of the foregoing are intended to be within the scope of the appended claims.

I claim:

1. A craniotomy drape comprising:

a main sheet having a fenestration;

an absorbent sheet layered on top of the main sheet, the absorbent sheet including a fenestration incident to the fenestration of the main sheet;

an incise sheet disposed between the main sheet and the absorbent sheet, the incise sheet including an adhesive side having a releasable layer disposed thereupon; and at least one gusset attached to a lateral anterior edge of the main sheet.

2. The craniotomy drape of claim 1, further comprising a fenestrated run-off pouch affixed to the absorbent sheet, with a back-side fenestration surrounding the fenestration of the main sheet, and a front-side fenestration.

3. The craniotomy drape of claim 2, wherein the run-off pouch includes a drain port, a solids screen, and a ductile material near the edge of the front-side fenestration.

4. The craniotomy drape of claim 3, wherein the ductile material is metal wire.

5. The craniotomy drape of claim 1, further comprising at least one tube holder attached either directly to the main sheet or to the absorbent sheet.

6. The craniotomy drape of claim 5, wherein the tube holder comprises an upper rectangular piece of a flexible material and a lower piece of a flexible material, wherein the upper and lower pieces are joined at a center line and wherein the upper piece has a hook and loop fastener arrangement on its outer edges, while the lower piece is secured either directly to the main sheet or to the absorbent sheet.

7. The craniotomy drape of claim 1, further comprising a main fold line going diagonally across the gusset.

8. A method of draping a patient for craniotomy procedures comprising using the craniotomy drape of claim 1.

* * * * *